US010625038B2

(12) United States Patent
Smith

(10) Patent No.: US 10,625,038 B2
(45) Date of Patent: Apr. 21, 2020

(54) MEDICO-SURGICAL APPARATUS AND METHODS

(71) Applicant: SMITHS MEDICAL INTERNATIONAL LIMITED, Kent (GB)

(72) Inventor: Peter Ryan Smith, Kent (GB)

(73) Assignee: Smiths Medical International Limited, Ashford, Kent (GB)

( * ) Notice: Subject to any disclaimer, the term of this patent is extended or adjusted under 35 U.S.C. 154(b) by 1123 days.

(21) Appl. No.: 14/649,254

(22) PCT Filed: Nov. 29, 2013

(86) PCT No.: PCT/GB2013/000519
§ 371 (c)(1),
(2) Date: Jun. 3, 2015

(87) PCT Pub. No.: WO2014/091178
PCT Pub. Date: Jun. 19, 2014

(65) Prior Publication Data
US 2015/0297851 A1 Oct. 22, 2015

(30) Foreign Application Priority Data
Dec. 15, 2012 (GB) .................................. 1222684.1

(51) Int. Cl.
A61M 16/04 (2006.01)
A61M 16/20 (2006.01)
(Continued)

(52) U.S. Cl.
CPC .... A61M 16/0468 (2013.01); A61M 16/0057 (2013.01); A61M 16/0463 (2013.01);
(Continued)

(58) Field of Classification Search
CPC .......... A61M 16/0465; A61M 16/0468; A61M 16/16; A61M 16/0057; A61M 16/0434;
(Continued)

(56) References Cited

U.S. PATENT DOCUMENTS 4,459,984 A * 7/1984 Liegner .................. A61F 2/203
128/207.15
4,773,412 A * 9/1988 Blom ...................... A61F 2/203
128/207.14
(Continued)

FOREIGN PATENT DOCUMENTS

EP         1 803 478      7/2007
WO         WO 86/02564    5/1986

OTHER PUBLICATIONS

PCT International Search Report and Written Opinion of the ISA/EP, PCT/GB2013/000519, dated Jun. 13, 2014.

Primary Examiner — Colin W Stuart
Assistant Examiner — Douglas Y Sul
(74) Attorney, Agent, or Firm — Louis Woo

(57) ABSTRACT

Apparatus for enabling speech while a tracheostomy tube is in place includes a tracheostomy tube 1 with a vocalisation gas lumen 15 extending along its length and opening at one end externally of the tube above the sealing cuff 10 in the trachea T. A ventilator 2 is connected to the main bore 3 of the tube 1 to supply ventilation gas cyclically to the patient. The ventilator 2 also has an auxiliary outlet 29 connected to the vocalisation gas lumen 15. The auxiliary outlet 29 supplies vocalisation gas to the vocalisation gas lumen 15 only during the expiratory phases of ventilation. Alternatively, the apparatus includes a separate supply 50 of vocalisation gas connected with the vocalisation gas lumen 15' via a valve 52. The valve 52 is controlled by pressure in the main gas supply tubing 31' so that the valve is opened to (Continued)

Figure 1:
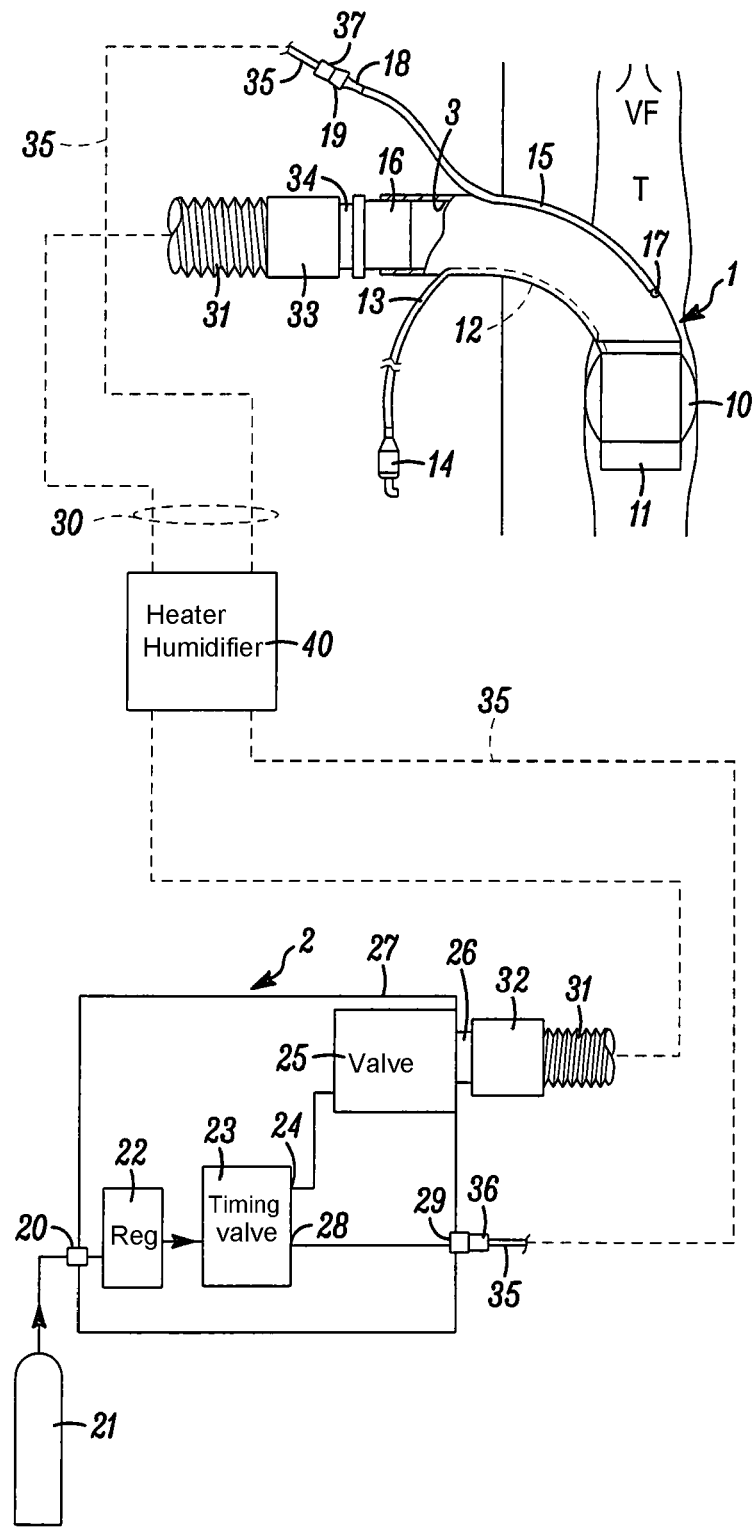

enable the supply of vocalisation gas only during the expiratory phases of ventilation.

10 Claims, 2 Drawing Sheets

(51) Int. Cl.
*A61M 16/00* (2006.01)
*A61M 16/16* (2006.01)
*A61M 16/12* (2006.01)

(52) U.S. Cl.
CPC ...... *A61M 16/0465* (2013.01); *A61M 16/122* (2014.02); *A61M 16/16* (2013.01); *A61M 16/201* (2014.02); *A61M 16/0434* (2013.01); *A61M 2202/02* (2013.01); *A61M 2205/3334* (2013.01); *A61M 2205/36* (2013.01)

(58) Field of Classification Search
CPC ............ A61M 16/201; A61M 16/0463; A61M 16/122; A61M 2202/02; A61M 2205/3334; A61M 2205/36

See application file for complete search history.

(56) References Cited

U.S. PATENT DOCUMENTS

| | | | |
|---|---|---|---|
| 5,515,844 A * | 5/1996 | Christopher | A61M 16/10 128/200.26 |
| 6,814,077 B1 | 11/2004 | Eistert | |
| 2008/0060646 A1* | 3/2008 | Isaza | A61M 16/0468 128/204.21 |
| 2009/0095302 A1* | 4/2009 | Blom | A61M 16/0465 128/207.16 |
| 2012/0097170 A1 | 4/2012 | Dawson | |
| 2012/0145156 A1* | 6/2012 | Lofaso | A61M 16/0468 128/205.24 |
| 2016/0038702 A1* | 2/2016 | Tanoue | A61M 16/0468 128/207.16 |

* cited by examiner

MEDICO-SURGICAL APPARATUS AND METHODS

This invention relates to apparatus of the kind including a tracheostomy tube, a source of ventilation gas and a source of vocalisation gas, the tube having a main bore connected with the source of ventilation gas by which ventilation gas is delivered to the patient and a gas lumen connected at one end with the source of vocalisation gas and opening at the opposite end on the outside of the tube in the trachea.

For various medical reasons a patient may need to be ventilated temporarily or permanently using a tracheostomy tube. One end of the tube is inserted in the trachea below the vocal folds and the other end emerges from a surgical opening in the neck. The patient end of the tube usually carries an inflatable sealing cuff on its external surface, which seals with the trachea when inflated, so that all ventilation gas flows along the tube. The external, machine end of the tube may be open to atmosphere or connected to a ventilator. While such a tube is inserted, because ventilation gas bypasses the vocal folds, it is not possible for the patient to speak. Tracheostomy tubes can be modified to enable some vocalisation by providing one or more openings or fenestrations in the upper surface of the tube midway along its length so that exhaled ventilation gas can enter the patient end of the tube and flow out through the fenestrations into the trachea and flow to the vocal cords. When not required, the fenestrations can be closed by an inner cannula inserted within the tube. A one-way valve may be attached to the machine end of the tube so that gas can flow into the tube through the machine end but the valve closes to prevent gas flow out of the machine end. In this way gas instead flows out of the fenestrations into the trachea and to the vocal folds. Such fenestrated tubes can work effectively where the patient has undamaged vocal folds and a lung capacity capable of producing sufficient flow of exhalation gas to cause the vocal folds to generate audible speech. In many cases, however, tracheostomy tubes are used to aid breathing by patients with compromised lung capacity, such as those suffering from COPD. These patients may not be able to generate sufficient exhalation gas flow to produce audible vocalisation. In order to alleviate this problem it is possible to use a tracheostomy tube having a gas conduit that extends along the tube from its machine end and opens on the outside of the tube above the sealing cuff. The gas conduit is connected to an external source of compressed air so that this is supplied continuously to the trachea and flows to the vocal folds to permit vocalisation. Such a tube is available from Smiths Medical International Limited under the trade mark Portex Vocalaid (Portex Vocalaid is a registered trade mark of Smiths Medical International Limited). The problem with such tubes that provide a continuous supply of vocalisation air is that the continuous air flow can be noisy and tends to cool and dry out the delicate tissue lining the upper trachea, which can lead to tissue trauma. Naturally, speech is not produced continuously but only during exhalation.

It is an object of the present invention to provide alternative apparatus.

According to one aspect of the present invention there is provided apparatus of the above-specified kind, characterised in that the source of vocalisation gas is arranged to deliver a higher rate of gas flow to the lumen during the expiratory phase of a ventilation cycle than during the inspiratory phase.

The source of vocalisation gas is preferably arranged to deliver vocalisation gas substantially only during the expiratory phase. The apparatus may include means for humidifying and warming the vocalisation gas. The source of ventilation gas may be provided by a main outlet of a ventilator by which a cyclical supply of ventilation gas is supplied to the main bore of the tracheostomy tube, the source of vocalisation gas being provided by an auxiliary outlet of the ventilator separate from the main outlet of the ventilator. Alternatively, the source of vocalisation gas may be provided by a vocalisation gas supply and a valve connected in line between the gas lumen and the vocalisation gas supply, the valve being arranged to be controlled by pressure of ventilation gas supplied to the tracheostomy tube such that the valve opens to allow flow of vocalisation gas when the pressure of ventilation gas is relatively low and closes when pressure of ventilation gas is relatively high.

According to another aspect of the present invention there is provided apparatus including a tracheostomy tube and a ventilator, the tracheostomy tube having a main ventilation bore, a vocalisation gas lumen opening at its patient end on the outside of the tube, and means connecting the main bore of the tube with a ventilation outlet of the ventilator, characterised in that the apparatus includes means connecting the machine end of the vocalisation gas lumen with an auxiliary outlet of the ventilator, and that the ventilator is arranged to supply cyclical vocalisation gas to its auxiliary outlet such that the vocalisation gas supplied to the vocalisation gas lumen is at a maximum during the expiratory phase of ventilation.

According to a further aspect of the present invention there is provided apparatus including a tracheostomy tube, a ventilator and a supply of vocalisation gas, the tracheostomy tube having a main ventilation bore and a vocalisation gas lumen opening at one end on the outside of the tube, first means connecting the main bore of the tube with the ventilator, and second means connected with the other end of the vocalisation gas lumen, characterised in that the apparatus includes a valve arrangement arranged to control flow from the vocalisation gas supply to the second means and the vocalisation gas lumen, and that the valve arrangement is operated in response to cycling of the ventilator such that gas flow to the vocalisation gas lumen is enabled preferentially during exhalation phases of ventilation.

According to a fourth aspect of the present invention there is provided a method of enabling speech by a patient including the steps of inserting a tracheostomy tube of the kind having a main bore by which ventilation gas is delivered to the patient and a vocalisation gas lumen extending along the tube from its machine end and opening externally of the tube within the trachea, characterised in that the method includes supplying vocalisation gas to the vocalisation gas lumen only during the expiratory phase of the ventilation.

Figure 2:
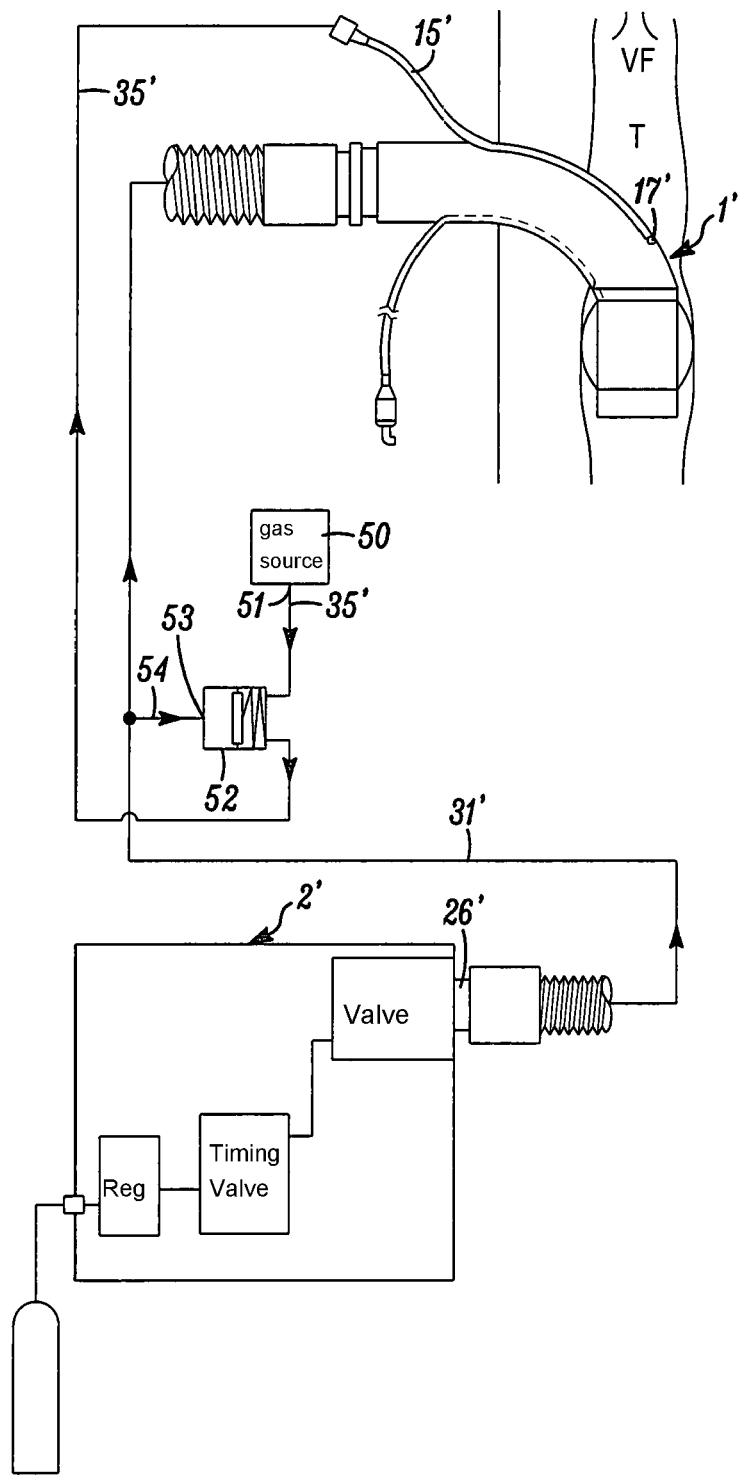

Two examples of apparatus according to the various aspects of the present invention will now be described, by way of example, with reference to the accompanying drawings, in which:

FIG. 1 shows schematically apparatus including a tracheostomy tube and a ventilator; and FIG. 2 shows schematically apparatus including a tracheostomy tube and a ventilator arranged differently from apparatus shown in FIG. 1.

With reference first to FIG. 1 there is shown a tracheostomy tube 1 connected with a ventilator 2 and arranged to supply vocalisation gas to the trachea T only during exhalation phases of ventilation.

The tube 1 may be a conventional tracheostomy tube with a main bore 3 along which ventilation gas is supplied to the patient and a sealing cuff 10 extending around it close to its patient end 11. The cuff 10 is inflated and deflated via an inflation lumen 12 extending along the length of the tube 1 around its inner curvature and opening into the cuff at its forward, patient end. The opposite end of the lumen 12 is provided by a small-bore inflation line 13 terminated by an inflation indicator balloon and connector 14 of the usual kind. A second small-bore, vocalisation lumen is provided by a small diameter tube 15 attached to the outer curvature of the tube 1 and this extends along the tube from close to its machine end 16 to a location just above the upper end of the sealing cuff 10 where it opens into the trachea T through a patient end opening 17. At its opposite, machine end 18 the tube 15 is terminated by a gas coupling 19. The tracheostomy tube 1 may be of the kind sold by Smiths Medical under the trade mark Portex Vocalaid (Portex Vocalaid is a registered trade mark of Smiths Medical).

The ventilator 2 has a gas input 20 connected to a source 21 of breathing gas at elevated pressure, such as a hospital air supply or a cylinder of compressed gas. Alternatively, the ventilator could include a pump and reservoir to produce its own supply of breathing gas. The input 20 connects with a regulator 22, which supplies gas at the desired pressure to a timing valve 23. The timing valve 23 has an adjustable time period, which can be set by the user as desired to produce a variable cycle of inspiratory and expiratory phases. The timing valve has two outlets, one of which 24 connects to a conventional patient valve 25, which provides a cyclical supply of inspiratory gas to a main gas outlet 26 on the housing 27 of the ventilator 2. The other outlet 28 of the timing valve 23 provides a gas output in intervals between the inspiratory phases (that is, during patient expiratory phases) to an auxiliary, vocalisation gas outlet 29 on the ventilator housing 27.

The tracheostomy tube 1 is connected with the ventilator 2 by a patient circuit 30. The circuit 30 includes flexible, corrugated, large bore tubing 31 extending between connectors 32 and 33 at opposite ends connected respectively with the main gas outlet 26 of the ventilator and a connector 34 fitted in the machine end 16 of the main ventilation bore 3 of the tracheostomy tube 1. The patient circuit 30 also includes a small-bore flexible tube 35 terminated at opposite ends by respective connectors 36 and 37 that are connected respectively to the vocalisation gas outlet 29 on the ventilator 2 and the gas coupling 19 at the machine end 18 of the vocalisation gas tube 15. The patient circuit 30 further includes an optional dual-channel heater and humidifier 40 connected in line with both the ventilation gas tubing 31 and the vocalisation gas tubing 35 so that gas supplied along both these paths is warmed and humidified.

It can be seen that, during the inspiratory phase of ventilation, the ventilator 2 supplies ventilation gas via the tubing 31 to the main bore 3 of the tube 1 so that it emerges from the patient end 11 of the tube to inflate the lungs. During this phase no gas (or negligible amounts of gas) is supplied to the vocalisation gas path 15. During the expiratory phase of ventilation, however, the ventilator 2 terminates supply of ventilation gas to the patient (or reduces this substantially) so that the patient can exhale through the tube 1 to atmosphere. At the same time, the ventilator 2 supplies a flow of breathing gas via the outlet 29 and the tubing 35 to the vocalisation gas lumen provided by the tube 15. This gas emerges from the opening 17 into the trachea T. The cuff 10 prevents this gas flowing into the bronchial system so it instead flows cephaladly up to the vocal folds VF to enable vocalisation and speech by the patient. By restricting the supply of vocalisation gas in this way to only the expiratory phases of ventilation, the noise caused by gas emerging from vocalisation opening 17 is restricted to the expiratory phases when it is more likely to be masked by the patient's speech. The patient is provided with vocalisation gas when he would normally speak, that is, during exhalation only. By confining the supply of vocalisation gas to expiratory phases only damage to the lining of the trachea caused by the drying and cooling effect of the flow of gas is minimised. This effect is further reduced if the vocalisation gas is warmed and humidified by the humidifier 40, as described above.

In some previous arrangements for enabling a patient with a tracheostomy tube to speak, the tracheostomy tube is formed with fenestrations in its wall or the cuff is deflated to allow exhaled gas to flow along the trachea beyond the tracheostomy tube to the vocal folds. However, many patients with severe respiratory damage are unable to generate sufficient flow of exhalation gas to produce audible speech. The arrangement described above can enable such patients to speak, although it is not confined to such patients.

It is not essential to use a modified ventilator to provide the supply of vocalisation gas. Instead, for example, the apparatus shown in FIG. 2 could be used. In FIG. 2 components similar to those in the apparatus of FIG. 1 are given the same reference number with the addition of a prime '. The ventilator 2' has a single outlet 26' via which cyclical breathing gas is supplied, that is, gas is supplied substantially only during the inspiratory phases. The gas flows to the main ventilation bore of the tube 1' via tubing 31'. The vocalisation line 15' of the tube 1' is connected via tubing 35' to a dedicated gas source 50, which provides a continuous supply of breathing gas at its outlet 51. The gas source for vocalisation could be derived from a location within the ventilator 2' where a continuous, non-cyclical gas flow is available. Preferably, the gas source 50 includes means for humidifying and warming the gas supplied to the outlet 51. The vocalisation tubing 35' is interrupted by a valve 52 that is operable to enable or prevent flow of gas along the tubing. The valve 52 is operated by gas pressure at a control inlet 53 such that a relatively high pressure at this inlet closes the valve, preventing flow along tubing 35'. When pressure at the control inlet 53 drops below a certain value the valve 52 opens to allow flow through the valve and along the vocalisation gas tubing 35'. The control inlet 53 is connected by a small-bore tube 54 to the main gas supply tubing 31' so that pressure in the main gas supply tubing is effective to switch the vocalisation tubing valve 52 on and off. More particularly, when the ventilator 2' supplies gas to the tube 1' via tubing 31' during the inspiratory phase, the pressure in the gas supply tubing is high causing the valve 52 to be held closed, thereby preventing any vocalisation gas emerging from the gas outlet 17' on the tube 1'. However, during the expiratory phase the ventilator output drops and pressure in tubing 31' falls below that sufficient to keep the vocalisation gas valve 52 closed. The vocalisation gas valve 52, therefore, opens to allow gas to flow from the gas source 50 via tubing 35' to emerge into the trachea T via the gas outlet 17' and thereby enable the patient to speak. The gas valve 52 need not be purely mechanical (driven by pressure in the tubing 31') but could instead be an electromechanical valve with a pressure sensor arranged to be responsive to pressure in tubing 31' so that the valve is moved electrically in response to sensed changes in pressure. This arrangement could be advantageous where gas flow or pressure changes in the breathing circuit are low.

This arrangement enables a conventional ventilator to be used with only some minor modification to the disposable patient tubing circuit.

It will be appreciated that, both with the apparatus shown in FIG. 1 and that shown in FIG. 2, it is not essential for vocalisation gas supply to be completely blocked during the inspiratory phase but only for the flow of gas to be reduced sufficiently to a level that prevents any significant damage to the tracheal lining and reduces noise. It might be preferable to allow a small flow of gas along the vocalisation tubing during the inspiratory phase to reduce the risk of any blockage of the tubing, such as by secretions produced within the trachea.

The invention claimed is:

1. Apparatus comprising a tracheostomy tube adapted to be placed in trachea of a patient, a source of ventilation gas and a source of vocalisation gas, the tube having a main bore connected with the source of ventilation gas by which ventilation gas is delivered to the tube for the patient and a gas lumen connected at one end with the source of vocalisation gas and opening at opposite end on outside of the tube in the trachea, characterised in that the apparatus includes a valve connected in line between the gas lumen and the source of vocalisation gas, the valve having a control inlet and is operationally responsive to the pressure of the ventilation gas at the control inlet such that when a relatively high pressure of the ventilation gas is at the control inlet the valve closes to prevent flow of vocalisation gas to the gas lumen, and when pressure of the ventilation gas at the control inlet falls to below a certain value the valve opens to allow flow of vocalisation gas to the gas lumen.

2. Apparatus according to claim 1, wherein the apparatus includes means for humidifying and warming the vocalisation gas.

3. Apparatus according to claim 1, wherein the source of ventilation gas is provided by a main outlet of a ventilator by which a cyclical supply of ventilation gas is supplied to the main bore of the tracheostomy tube, and that the source of vocalisation gas is provided by an auxiliary outlet of the ventilator separate from the main outlet of the ventilator, and that the valve is within the ventilator and is arranged to switch gas supply between either the main outlet or the auxiliary outlet.

4. Apparatus according to claim 1, wherein the ventilation gas is supplied to the tracheal tube.

5. Apparatus according to claim 1, characterised in that the valve is opened to deliver vocalisation gas substantially only during the expiratory phase.

6. Apparatus according to claim 1, wherein the valve is an electro-mechanical valve with a pressure sensor arranged to be responsive to pressure of ventilation gas.

7. Apparatus comprising a tracheostomy tube and a ventilator, the tracheostomy tube having a main ventilation bore, a vocalisation gas lumen opening at its patient end on outside of the tube, and a bore tubing connecting the main bore of the tube with a ventilation outlet of the ventilator, wherein the apparatus includes a vocalisation tubing connecting machine end of the vocalisation gas lumen with an auxiliary outlet of the ventilator, a valve connected in line between the gas lumen and the auxiliary outlet, the valve having a control inlet and is operationally responsive to the pressure of the ventilation gas at the control inlet such that when a relatively high pressure of the ventilation gas is at the control inlet the valve closes to prevent flow of vocalisation gas to the gas lumen, and when pressure of the ventilation gas at the control inlet falls to below a certain value the valve opens to allow vocalisation gas to be supplied to the vocalisation gas lumen during expiratory phase of ventilation.

8. Apparatus according to claim 7, wherein the valve is an electro-mechanical valve with a pressure sensor arranged to be responsive to pressure of ventilation gas.

9. Apparatus comprising a tracheostomy tube, a ventilator and a supply of vocalisation gas, the tracheostomy tube having a main ventilation bore and a vocalisation gas lumen opening at one end on outside of the tube, first means connecting the main bore of the tube with the ventilator, and second means connected with the end of the vocalisation gas lumen, wherein the apparatus includes a valve arrangement arranged to control flow from the vocalisation gas supply to the second means and the vocalisation gas lumen, and that the valve arrangement includes a valve operationally responsive to cycling of the ventilator, the valve having a control inlet and is operationally responsive to the pressure of the ventilation gas at the control inlet such that when a relatively high pressure of the ventilation gas is at the control inlet, the valve terminates or at least reduce substantially gas flow from the ventilator to the main ventilation bore and when pressure of the ventilation gas at the control inlet falls to below a certain value, the valve opens to allow flow of vocalisation gas to the gas lumen such that gas flow to the vocalisation gas lumen is enabled during exhalation phases of ventilation.

10. Apparatus according to claim 9, wherein the valve is an electro-mechanical valve with a pressure sensor arranged to be responsive to pressure of ventilation gas.

* * * * *